US009861527B2

(12) United States Patent
Fu et al.

(10) Patent No.: US 9,861,527 B2
(45) Date of Patent: Jan. 9, 2018

(54) ROBUST LASER CUTTING METHODS FOR OPHTHALMIC SURGERY

(71) Applicant: AMO Development, LLC., Santa Ana, CA (US)

(72) Inventors: Hong Fu, Irvine, CA (US); John M. Tamkin, San Marino, CA (US)

(73) Assignee: AMO Development, LLC, Santa Ana, CA (US)

(*) Notice: Subject to any disclaimer, the term of this patent is extended or adjusted under 35 U.S.C. 154(b) by 130 days.

(21) Appl. No.: 14/157,047

(22) Filed: Jan. 16, 2014

(65) Prior Publication Data
US 2014/0200563 A1 Jul. 17, 2014

Related U.S. Application Data

(60) Provisional application No. 61/753,319, filed on Jan. 16, 2013.

(51) Int. Cl.
A61F 9/00 (2006.01)
A61F 9/008 (2006.01)

(52) U.S. Cl.
CPC ........ *A61F 9/0084* (2013.01); *A61F 9/00827* (2013.01); *A61F 9/00836* (2013.01);
(Continued)

(58) Field of Classification Search
CPC .... A61F 9/008; A61F 9/0084; A61F 9/00827; A61F 9/00836; A61F 2009/0087; A61F 2009/00889; A61F 2009/00897
(Continued)

(56) References Cited

U.S. PATENT DOCUMENTS 4,764,930 A   8/1988  Bille et al.
5,549,632 A   8/1996  Lai
(Continued)

FOREIGN PATENT DOCUMENTS

DE   102009012873 A1      9/2010
DE   102011085046 A1 *    4/2013   ......... A61F 9/00825
(Continued)

OTHER PUBLICATIONS

International Search Report and Written Opinion for Application No. PCT/US2014/011848, mailed on May 9, 2014, 12 pages.
(Continued)

Primary Examiner — Lynsey Eiseman
Assistant Examiner — Dacheng Xie
(74) Attorney, Agent, or Firm — Abbott Medical Optics Inc.

(57) ABSTRACT

A method and apparatus for performing ophthalmic laser surgery using a pulsed laser beam is provided. The method includes establishing an initial cutting pattern comprising a plurality of original photodisruption points, establishing an enhanced cutting pattern comprising a plurality of enhanced photodisruption points selected to decrease potential adverse effects due to patient movement and having increased density over a fixed area as compared with the plurality of original photodisruption points, and performing an ocular surgical procedure according to the enhanced cutting pattern. Enhanced cutting patterns may include circular cuts around the periphery of a capsule, vertical side cuts for lens fragmentation, raster lamellar cuts, and grid lamellar cuts. Each photodisruption point in the initial cutting pattern and the enhanced cutting pattern comprises a laser target point.

2 Claims, 7 Drawing Sheets

(52) U.S. Cl.
CPC .............. *A61F 2009/0087* (2013.01); *A61F 2009/00889* (2013.01); *A61F 2009/00897* (2013.01)

(58) Field of Classification Search
USPC ....................................................... 606/2–19
See application file for complete search history.

(56) References Cited

U.S. PATENT DOCUMENTS

| | | | |
|---|---|---|---|
| 5,993,438 A | 11/1999 | Juhasz et al. | |
| 2006/0118263 A1 | 6/2006 | Silvestrini | |
| 2009/0088734 A1* | 4/2009 | Mordaunt | A61B 18/20 606/13 |
| 2010/0174274 A1* | 7/2010 | Bille | A61F 9/008 606/5 |
| 2011/0022036 A1 | 1/2011 | Frey et al. | |
| 2012/0016352 A1* | 1/2012 | Dick | A61F 9/008 606/5 |
| 2014/0257259 A1* | 9/2014 | Papastathopoulos | A61F 9/00825 606/4 |

FOREIGN PATENT DOCUMENTS

| | | | | |
|---|---|---|---|---|
| EP | 1977725 A1 | 10/2008 | | |
| WO | WO-2012135073 A2 | 10/2012 | | |
| WO | WO 2013057318 A1 * | 4/2013 | ......... | A61F 9/00825 |

OTHER PUBLICATIONS

Extended European Search Report for Application No. EP14199237, mailed on Mar. 7, 2016, 6 pages.
European Search Report for Application No. EP17156854, dated Jun. 21, 2017, 6 pages.

* cited by examiner

ROBUST LASER CUTTING METHODS FOR OPHTHALMIC SURGERY

CROSS REFERENCE TO RELATED APPLICATIONS

This application claims the benefit of priority to U.S. Provisional Application No. 61/753,319, filed Jan. 16, 2013, the entire content of which is incorporated herein by reference.

BACKGROUND

I. Field

This invention generally relates to the field of ophthalmic surgery, and more particularly to particular cutting techniques and methods used during ophthalmic laser surgery, including cataract and refractive surgeries.

II. Background

Vision impairments such as myopia (i.e. near-sightedness), hyperopia (i.e. far-sightedness), and astigmatism can be corrected using eyeglasses or contact lenses. Alternatively, ophthalmic surgery can be used to address these same problems. Eye surgery is also commonly used to treat conditions such as cataracts, which, if left untreated, may cause blurred vision and/or blindness.

Laser surgery is becoming a preferred technique for ophthalmic procedures as a laser is generally more precise and accurate when compared to manual surgical tools. In laser refractive surgery, such as the commonly known LASIK (Laser Assisted in Situ Keratomileusis) procedure, a surgeon uses a laser to reshape the cornea. The LASIK procedure has three steps, namely: (1) preparation of a corneal flap; (2) ablation of the corneal stroma with an excimer laser; and (3) repositioning the flap.

Previously, a microkeratome was used for corneal flap cutting and preparation, but these days, it is more common to use a non-ultraviolet (UV) laser that emits radiation with ultra-short pulse durations in the femtosecond or picosecond range. Besides cutting corneal flaps, pulsed lasers are also useful for making incisions in the corneal stroma to correct astigmatism. Ophthalmic lasers provide improvements over microkeratomes as more patients achieve an improved level of post-operative visual acuity in the months after surgery. Further, laser surgery tends to lessen the chance of irregular, imprecise, and inaccurate cuts and related complications.

Non-ultraviolet, ultra-short pulsed lasers are also being used for cataract surgery, including capsulotomy procedures. During cataract surgery, a pulsed laser beam may be used to create an initial incision in the cornea, to create openings in the anterior or posterior capsular bag for capsulotomy, as well as to crack or break-up the clouded cataractic lens. For example, a pulsed laser beam can be used to create an opening in the anterior capsule for an anterior capsulotomy procedure to allow access to the cataractic lens. Sometimes, a posterior capsulotomy procedure is required after cataract surgery when the posterior capsule becomes cloudy and causes vision problems. In posterior capsulotomy, the pulsed laser can be used to create an opening in a clouded posterior capsule, thereby allowing light to pass freely through the opening. In both types of capsulotomies, pulsed laser systems reduce the possibility of irregular, inaccurate, and imprecise incisions and related complications that may occur with manual surgical techniques.

Laser eye surgeries are generally performed while the patient is awake. Because a patient's eye movement can reduce the procedure's accuracy and precision, the laser system needs to compensate for and/or reduce or stabilize eye movement. One approach to do so uses an eye stabilizing device, such as a patient interface that physically attaches to the patient's eye and prevents movement. Typically, the patient interface is attached to the eye using mechanical pressure, such as vacuum suction, which can be uncomfortable for the patient, and may even cause post-operative pain and scarring. Thus, certain alternate devices have been proposed to compensate for eye movement. These include an eye tracker, which tracks the position of the eye during surgery, and provides the system with real time signals about eye position. The laser system then uses the position information from the eye tracker to adjust or reposition the laser beam before making an incision. To ensure accuracy and precision, the trajectory of the laser beam's focus must be corrected in real time to compensate for eye movement monitored by the eye tracker. But, there are delays inherent to eye trackers and their interactions with the laser system. Because the eye tracker and the laser beam delivery mechanics tend to introduce positional errors due to latency between eye movement and laser adjustment, the resulting incision pattern in the eye may deviate from that which is programmed or desired. These can result in less than ideal incisions.

Therefore, it would be beneficial to provide a pulsed laser surgical system that uses an eye tracker and allows the laser beam to make robust and accurate incisions despite eye tracker/laser beam adjustment latency issues.

SUMMARY

An objective of this invention is to provide a laser ophthalmic system that uses an eye tracker and allows the laser beam to make robust and accurate incisions despite latency between the eye tracker and laser beam adjustment, which substantially obviates one or more problems due to limitations and disadvantages of the related art. To achieve this and other advantages, an embodiment of the present design provides a method for performing an ophthalmic laser surgery using a non-ultraviolet ultra-short pulsed laser system. The method includes establishing an initial cutting pattern comprising a plurality of original photodisruption points, establishing an enhanced cutting pattern comprising a plurality of enhanced photodisruption points selected to decrease potential adverse effects due to patient movement and having increased density over a fixed area as compared with the plurality of original photodisruption points, and performing an ocular surgical procedure according to the enhanced cutting pattern. Each photodisruption point in the initial cutting pattern and the enhanced cutting pattern comprises a laser target point. Examples of cutting patterns may include circular cuts around the periphery of a capsule, vertical side cuts for lens fragmentation, raster lamellar cuts, and grid lamellar cuts. Various aspects and features of the disclosure are described in further detail below.

The above summary and the following detailed description are merely exemplary, illustrative, and explanatory, and are not intended to limit, but to provide further explanation of the invention as claimed. Additional features and advantages of the invention will be set forth in the descriptions that follow, and in part, will be apparent from the description, or may be learned by practicing various embodiments of the invention. The objectives and other advantages of the invention will be realized by the structures and methods particu-

DETAILED DESCRIPTION

The following detailed description is merely illustrative and exemplary in nature and is not intended to limit the embodiments of the subject matter or the application, and uses of such embodiments. As used in this disclosure, the words "exemplary" and "illustrative" mean "serving as an example, instance, or illustration." Any implementation described as exemplary or illustrative is not meant to be necessarily construed as preferred or advantageous over other implementations. Further, there is no intention to be bound by any expressed or implied theory presented in the preceding background of the invention, brief summary, or the following detailed description.

Figure 1:
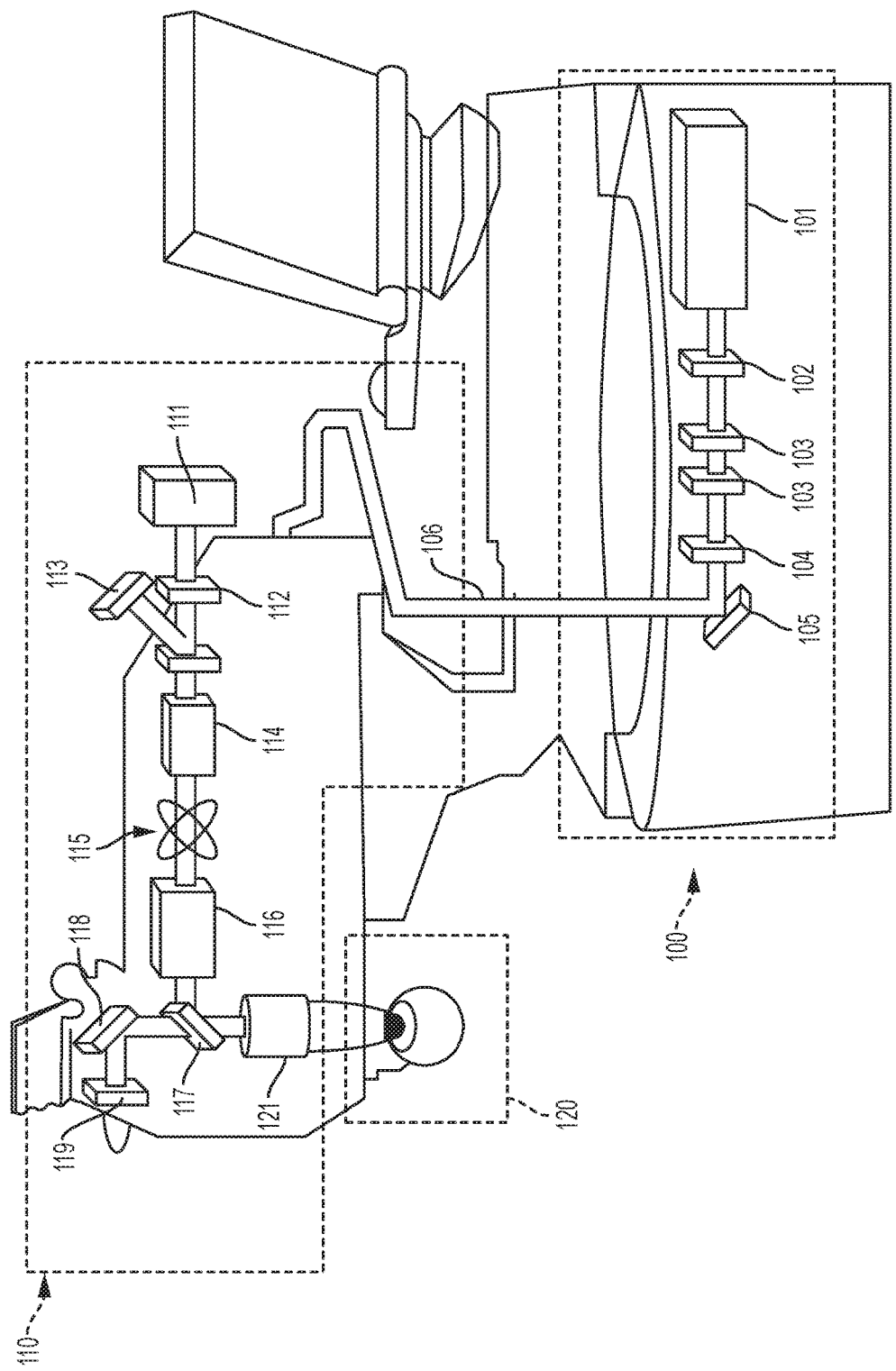
FIG. 1 illustrates a general overview of a pulsed laser system configured to employ an embodiment of the present design.

FIG. 1 illustrates a general overview of a non-ultraviolet pulsed laser system configured to employ an embodiment of the present design. In FIG. 1, laser engine 100 includes laser source 101 which provides laser light in ultra-short pulses to variable attenuator 102 configured to attenuate the beam, and energy monitors 103 to monitor beam energy level, and first safety shutter 104 serving as a shutoff device if the beam is unacceptable. Beam steering mirror 105 redirects the resultant laser beam to the beam delivery device 110, through articulated arm 106 to range finding camera 111. The range finding camera 111 determines the range needed for the desired focus at the eye 120. Beam delivery device 110 includes second safety shutter 112 and beam monitor 113, beam pre-expander 114, X-Y (position) scanner 115, and zoom beam expander 116. Zoom beam expander 116 expands the beam toward IR mirror 117 which reflects and transmits the received beam. Mirror 118 reflects the received beam to video camera 119, which records the surgical procedure on the eye 120. IR mirror 117 also reflects the laser light energy to objective lens 121, which focuses the laser light energy to eye 120.

In ophthalmic surgery, a non-ultraviolet (UV), ultra-short pulsed laser can produce pulsed laser beams having pulse durations measured in femtoseconds. Such a device as shown in FIG. 1 can provide an intrastromal photodisruption technique for reshaping the cornea using a non-UV, ultra-short (e.g., femtosecond or picosecond pulse duration), pulsed laser beam produced by laser source 101 that propagates through corneal tissue and is focused at a point below the surface of the cornea to photodisrupt stromal tissue at the focal point. The focusing optics, such as beam pre-expander 114, zoom beam expander 116, IR mirror 117 and objective lens 121, direct the pulsed laser beam toward an eye 120 (e.g., onto or into a cornea) for plasma mediated (e.g., non-UV) photoablation of superficial tissue, or into the stroma of the cornea for intrastromal photodisruption of tissue. In this embodiment, the system may also include a lens to change the shape (e.g., flatten or curve) of the cornea prior to scanning the pulsed laser beam toward the eye. The system is capable of generating the pulsed laser beam with physical characteristics similar to those of the laser beams generated by a laser system disclosed in U.S. Pat. No. 4,764,930, U.S. Pat. No. 5,993,438, or the like.

The ophthalmic laser system can produce an ultra-short pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam has a wavelength that permits the pulsed laser beam to pass through the cornea without absorption by the corneal tissue. The wavelength of the pulsed laser beam is generally in the range of about 3 µm to about 1.9 nm, preferably between about 400 nm to about 3000 nm, and the irradiance of the pulsed laser beam for accomplishing photodisruption of stromal tissues at the focal point is typically greater than the threshold for optical breakdown of the tissue. Although a non-UV, ultrashort pulsed laser beam is described in this embodiment, the pulsed laser beam may have other pulse durations and different wavelengths in other embodiments. Further examples of devices used in performing ophthalmic laser surgery are disclosed in, for example, U.S. Pat. Nos. 5,549,632, 5,984,916, and 6,325,792, the contents of each of which are each incorporated herein by reference.

Figure 2:
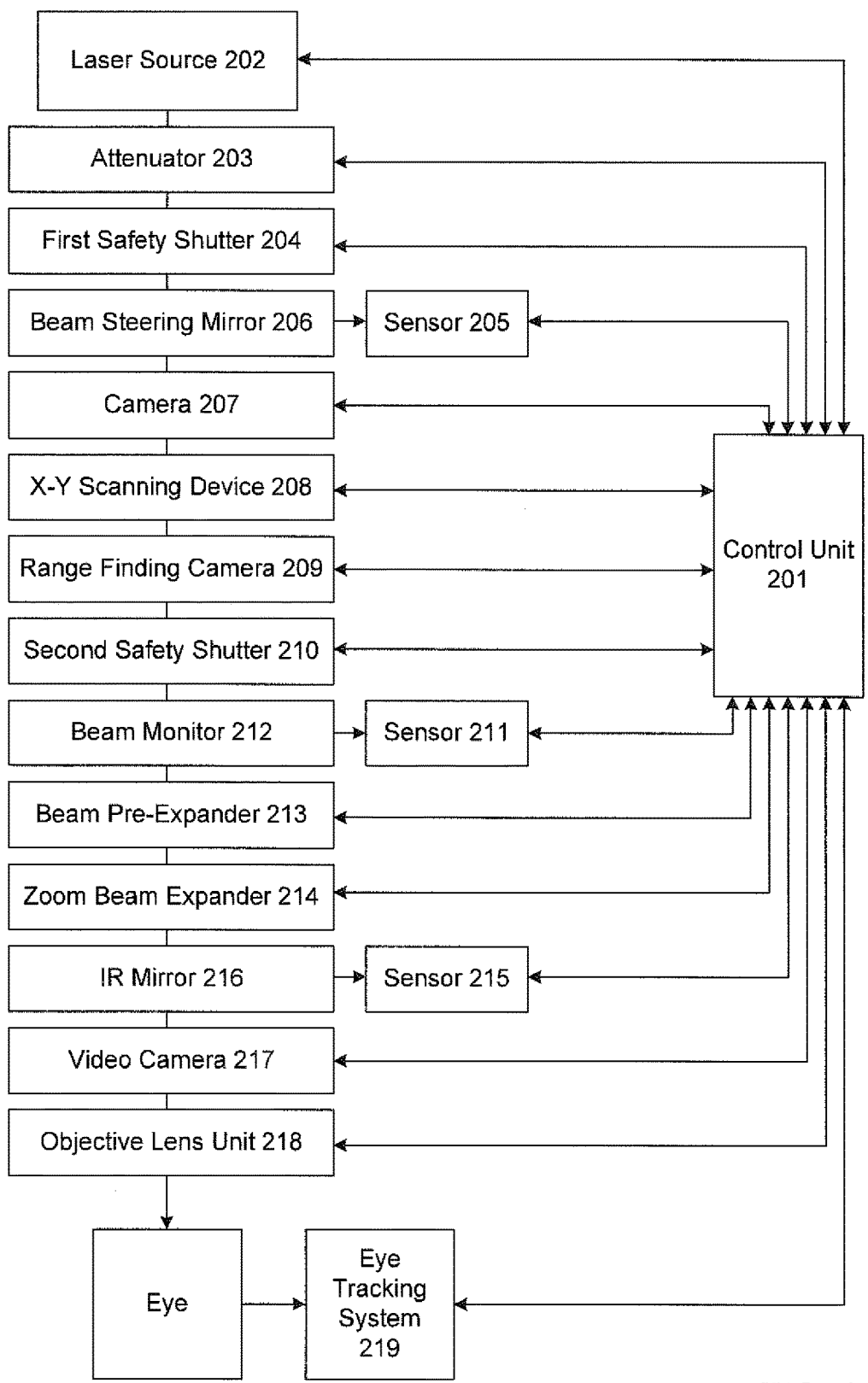
FIG. 2 is a general diagram including a controller configured to control various components illustrated in FIG. 1.

FIG. 2 illustrates a general diagram including a controller configured to control various components illustrated in FIG. 1. Not shown in FIG. 1 is an eye tracker typically used and placed on or adjacent to the eye to track eye movements. A series of sensors may be provided to sense beam diameter, location, and intensity at the various mirrors provided. FIG. 2 shows a control unit 201 configured to interface with the laser source 202 to transmit the laser, the attenuator 203 to attenuate the laser beam, the first safety shutter 204 to enable shutoff in extreme circumstances, a sensor 205 provided with beam steering mirror 206, and camera 207. The control unit 201 also interfaces with the x-y scanning device 208 to enable x-y scanning of the beam delivery device, and controls range finding camera 209, second safety shutter 210, a sensor 211 attached to beam monitor 212, the beam pre-expander 213, zoom beam expander 214, and the sensor 215 attached to IR mirror 216. The control unit 201 interfaces with video camera 217 and objective lens unit 218 which contains the objective lens, and eye tracking system 219.

The present design seeks to control the position of the laser with respect to the eye and provide patterns and techniques that enable more robust cuts than previous systems and methods allowed. Certain techniques using eye tracking systems have been used in the past to make specific cuts. But, because there is latency between the tracking system 219 and the control unit 201 sensing eye movement, and the beam delivery device adjusting position of the beam to compensate for such movement, the resulting cuts may be imprecise.

In ophthalmic surgery using a non-ultraviolet, pulsed laser beam, a tissue cut is realized when a 2D array of microscopic photodisruption points are connected by the emitted beam, resulting in a macroscopic tissue separation. The present design uses an enhanced laser treatment pattern so that the tolerance for microscopic positional deviations of photodisruption points is increased and the likelihood of intended macroscopic tissue separation is improved.

Based on an existing pattern of photodisruption points, the present design establishes an enhanced pattern that increases the probability that nearest-neighbor photodisruption points will connect. As part of the enhanced pattern, the present design places secondary, backup, or redundant photodisruption points such that multiple connections are available between the photodisruption points, thus increasing the likelihood that sufficient connections exist among the photodisruption points to result in the intended macroscopic tissue separation even in the presence of positional errors.

The present design includes descriptions of various patterns of photodisruption points. However, the design is not specifically limited to the techniques and patterns disclosed herein. Various other patterns and designs may be used as ocular surgery can change depending on a variety of circumstances and new techniques. In general, however, the specific patterns employed are intended to provide robust cuts depending on a number of variables, including the surgical needs, the desired cut shape and orientation, the range of actual and potential position errors, the eye movement characteristics, the laser depth of focus, and the laser pulse rate.

In laser ophthalmic surgery, it is generally understood that virtually any laser position can be attained by device and laser beam movement in addition to the precision focus mechanisms available to the laser. In this regard, a number of different patterns and positions can be executed or attained. While primarily discussed with respect to making certain cuts, it is to be understood the present design may also be employed to perform fragmentation or chopping of a lens.

Figure 3C:
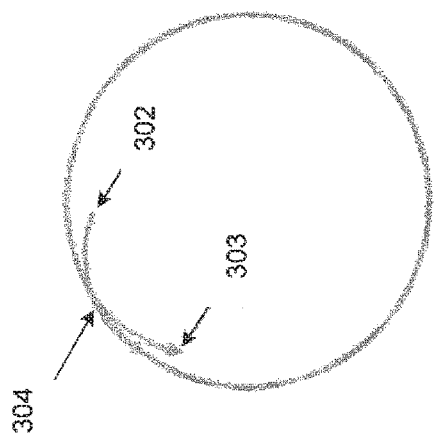
FIGS. 3A-3C illustrate a first general cutting technique for use in a capsulotomy during laser cataract surgery.
Figure 3B:
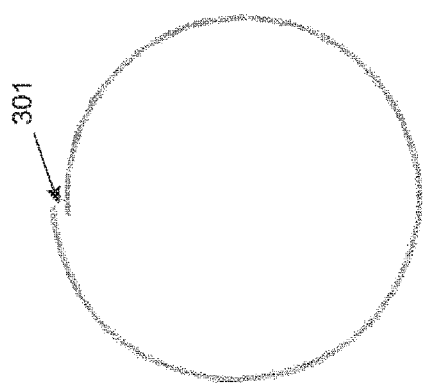
Figure 3A:
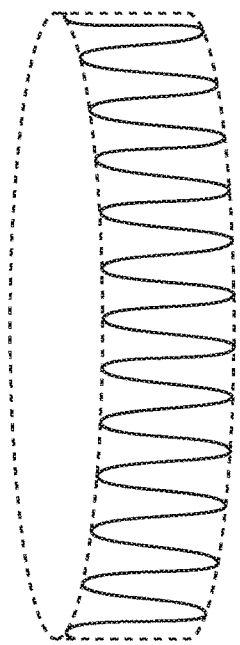

FIGS. 3A-3C illustrate a first general cutting technique for use in a capsulotomy during laser cataract surgery. FIG. 3A is a side view of a capsule region desired to be cut, wherein a cut resembling a sine wave is employed around the outside or periphery of the capsule region. In FIG. 3A, the laser scans in the z-direction in a depth range of a certain number of micrometers, i.e. scans up and down an approximately equal distance in micrometers around the periphery of the capsule. If a patient moves his or her eye during this procedure, there is a possibility that the cut will not close or complete.

FIG. 3B is a top view of one such scan where patient movement results in the pattern not being completed, i.e. the end of the pattern does not meet the beginning of the pattern and thus leaves an uncut gap 301, resulting in incomplete separation and tear of the capsule material. FIG. 3C shows an improved scan according to the present design, wherein the pattern is altered such that overlap exists, i.e. the side cut is over 360 degrees. In this arrangement, the side cut forms a closed loop. Hence in this embodiment, an initial pattern is contemplated, here having a 360 degree profile, and an improved pattern is established, here a greater than 360 degree pattern, going from a revised start point 302, cutting according to the pattern, and ending at a revised end point 303 resulting in a greater than 360 degree cut. The result is a likely cut with an overlap at or around point 302.

In the drawings, the photodisruption points that are pictured represent desired target points for the laser and not the actual cuts or incisions, which may differ in size and shape and may be slightly off-set from the photodisruption points pictured.

Thus the design of FIGS. 3A-3C can be thought of as having one disruption point as a baseline cut pattern, and a revised or enhanced cut pattern that includes two disruption points, the start and end point in FIG. 3C, selected to increase the likelihood of a complete cut and decrease potential adverse effects due to patient movement.

Figure 4A:
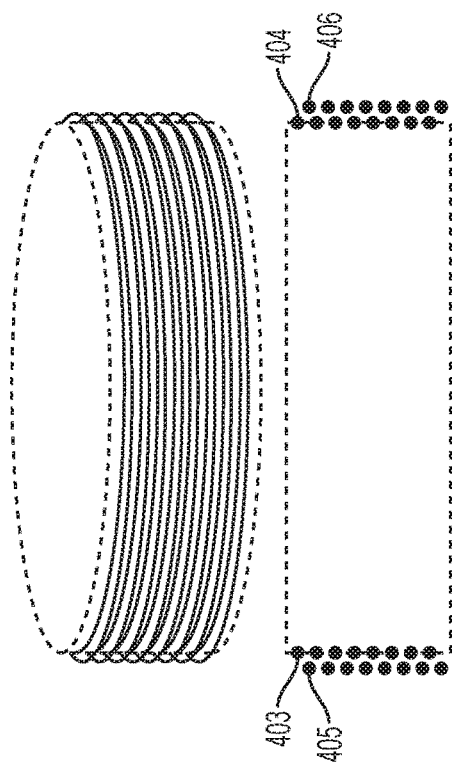
FIGS. 4A and 4B illustrate a second capsulotomy procedure.
Figure 4B:
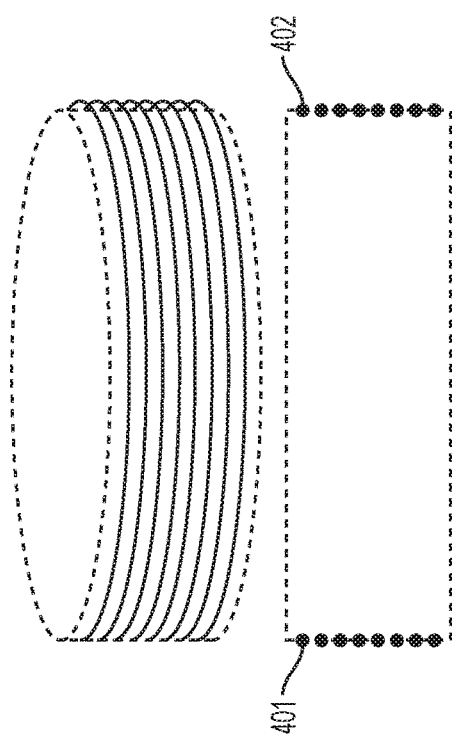

FIGS. 4A and 4B illustrate a second capsulotomy procedure. The top of FIG. 4A is a side perspective view of the capsule while the bottom of FIG. 4A is a side view of the capsule. The top view of FIG. 4A illustrates a series of circles used to cut the capsule in a series of slices. The bottom view is a side cut-away view illustrating the various photodisruption points in the circular pattern. In FIG. 4A, the laser cuts a circle from point 401 to point 402 and back around to point 401, and then proceeds to the next cut. In the presence of position errors, this circular laser cutting trajectory will not return to a point exactly beneath or above the previous turn, potentially resulting in no connectivity between turns forming the cut, and therefore, an incomplete cut.

FIG. 4B illustrates a spiral pattern for a capsulotomy wherein a series of additional photodisruption points are established, in this arrangement both vertically and horizontally offset from the prior set of photodisruption points, i.e. the baseline pattern of FIG. 4A. In operation, a cut is made around the capsule at points 403 and 404, and the laser proceeds to a cut around the capsule at points 405 and 406, and progresses in this manner via all the remaining points. Thus, the design of FIGS. 4A and 4B provide a baseline cut pattern and a modified or enhanced cutting pattern including an additional number of photodisruption or cut points selected to provide an enhanced likelihood of tissue separation in the presence of position errors.

Figure 5B:
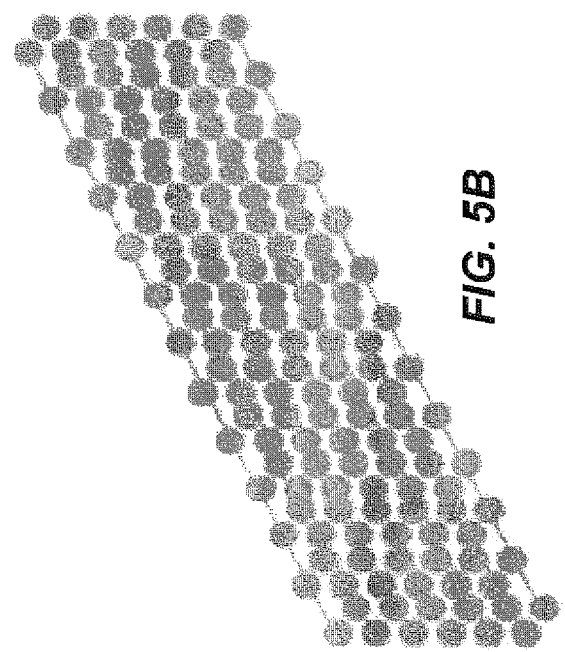
FIGS. 5A and 5B illustrate a further embodiment of the present design for use in performing a vertical side cut.
Figure 5A:
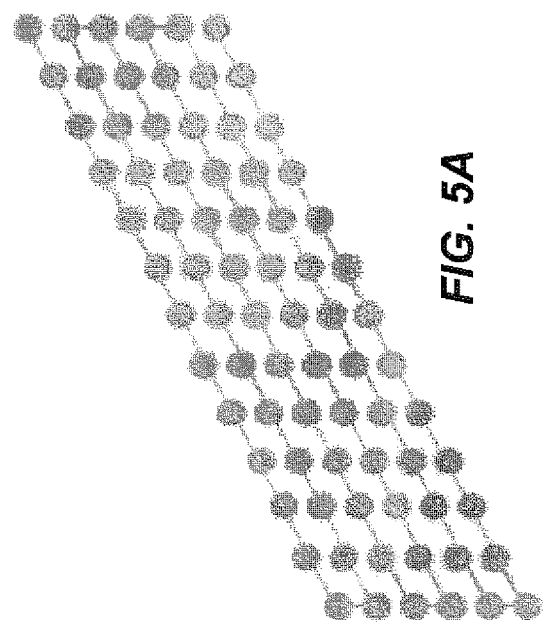

FIGS. 5A and 5B illustrate a further embodiment of the present design for use in a vertical side cut, useful in lens fragmentation and typically employed during refractive surgery to create a corneal flap. From FIG. 5A, a single layer vertical cut is provided, with a series of photodisruption points. As is understood to those skilled in the art, the photodisruption points represent points where the laser is focused, and use of the laser at such photodisruption points causes penetration of the tissue and adjacent points are in sufficient proximity to prevent tearing, i.e. a small enough amount of tissue remains such that the tissue separates and a cut made. In the depiction of FIG. 5A, the laser progresses sequentially through each of the diagonal lines presented. Again, such a pattern is sensitive to position error in that movement of the eye can result in an incomplete or inadequate cut.

FIG. 5B illustrates a multi-layered vertical side cut in accordance with the present design, wherein additional disruption points are provided at an offset, both vertically and horizontally, from the baseline cut pattern of FIG. 5A. This enhanced multi-layered vertical side cut pattern may be traversed in different ways using the ultra-short pulsed laser, such as going over and cutting a first (topmost) diagonal line, followed by a cut of a second (lower) diagonal line, and progressing sequentially downward through successive diagonal lines. Thus, the present embodiment includes establishing a baseline cut pattern and adding a series of photodisruption points to the baseline profile selected to provide an enhanced likelihood of tissue separation in the presence of position errors.

Figure 6A:
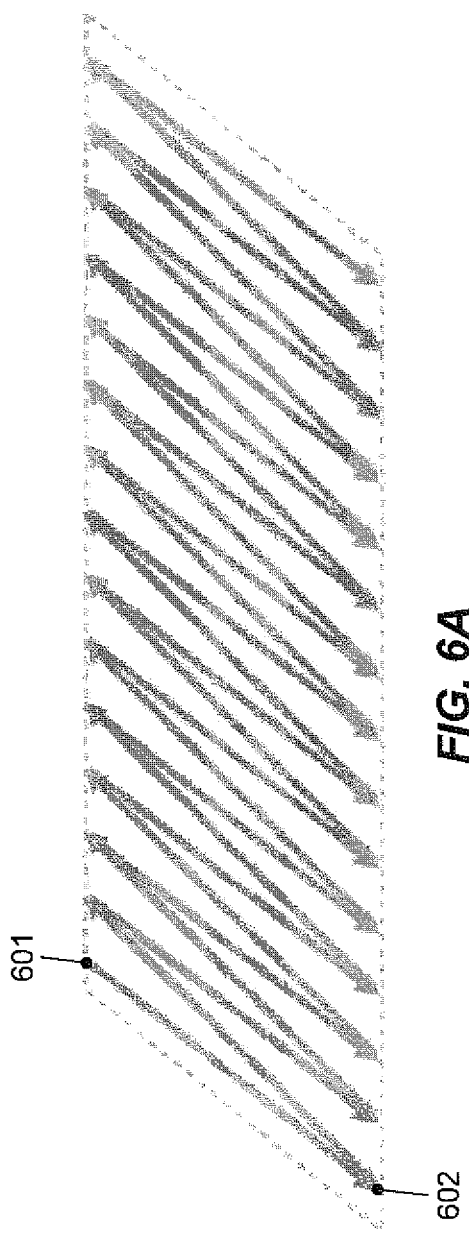
FIGS. 6A and 6B show a raster lamellar cut pattern.
Figure 6B:
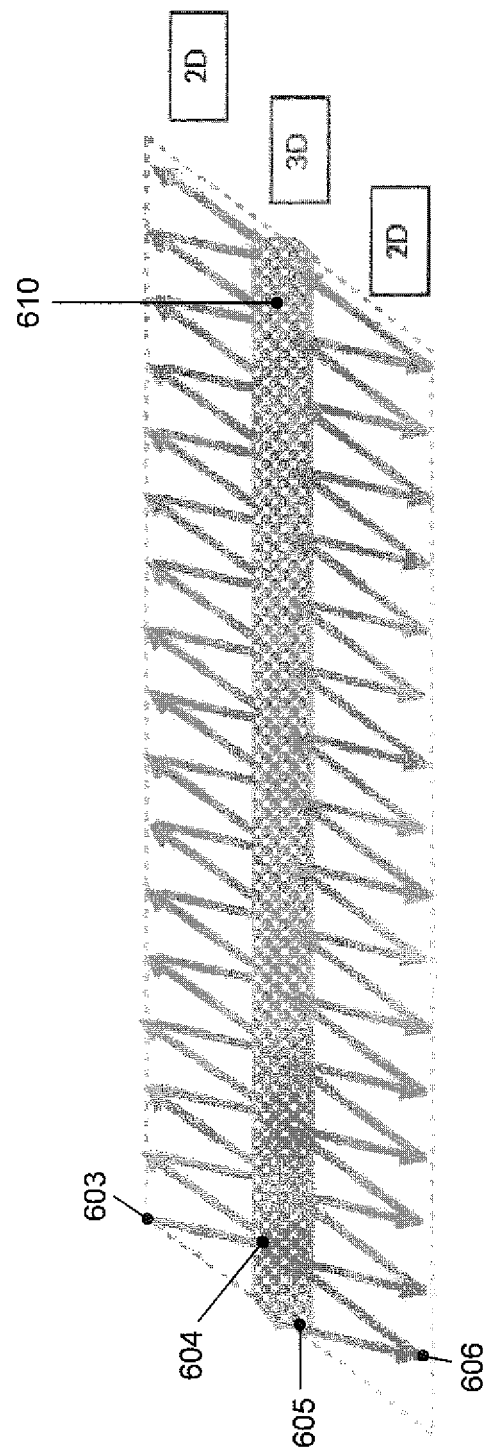

FIGS. 6A and 6B illustrate a raster lamellar cut for lens fragmentation according to the present design. FIG. 6A shows a baseline raster laser cutting pattern comprising a series of linear cuts to a plurality of points, such as upper point 601 and lower point 602. Such a linear cutting profile is subject to positional errors, possibly resulting in portions of the pattern being uncut, with an increased risk of tearing. The time to complete one raster scan, such as a scan from point 601 to 602, is generally less than 10 milliseconds, and this can be enough time to result in positional errors if the eye moves.

FIG. 6B illustrates a raster scan with two sets of cuts and two sets of photodisruption points, including upper first point 603 and upper second point 604, and lower first point 605 and lower second point 606. The time to complete one scan, i.e. from upper first point 603 to upper second point 604, is typically much less than 10 milliseconds. A briefer traversal of the raster pattern, and a smaller raster pattern used, results in a reduction in the likelihood of position error. Using the pattern of FIG. 6B, the two halves of the raster period (upstroke/downstroke) will more likely connect even in the presence of eye movement.

For the case of a longer depth of laser focus, which depends on the system's numerical aperture, the two raster patterns tend to be thick in the z-direction, and will be connected when there is an overlap between the two shorter raster patterns shown in FIG. 6B. However, if the depth of focus is small, the system can apply a three dimensional (3D) laser pattern or laser pattern array, shown as pattern 610, to reliably connect the two raster patterns to result in big lamellar cut.

From FIG. 6B, it is apparent that the disruption points 604 in the upper raster scan and 605 in the lower raster scan enter, in this view, the 3D region, pattern 610. A different sized 3D region, pattern 610 that touches the end points of a raster scan or raster scans that do not touch or barely touch the 3D region may be used. In general, overlap between the raster scans and the 3D pattern can provided enhanced likelihood of successful cutting. Thus, the present embodiment comprises again establishing a baseline pattern and providing an increased number of photodisruption points designed or intended to increase likelihood of a robust cut, or decrease the potential effects of position errors.

Figure 7B:
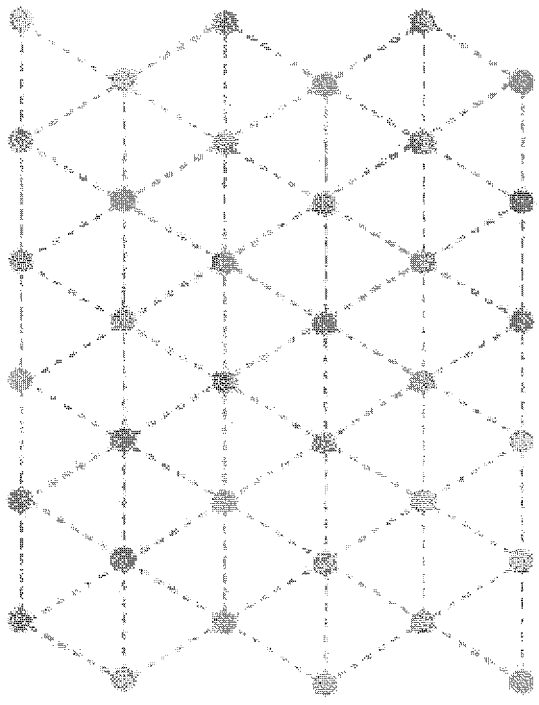
FIGS. 7A and 7B illustrate an arrangement for performing a lamellar cut for a corneal flap which is created to expose the corneal stroma in laser refractive surgery.
Figure 7A:
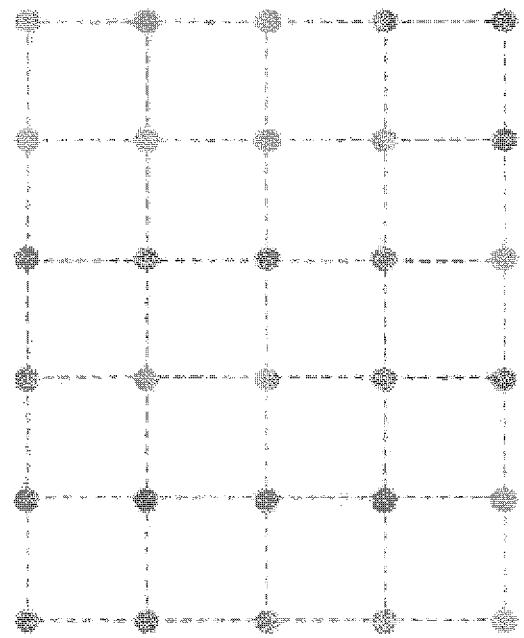

FIGS. 7A and 7B illustrate an arrangement for performing a lamellar laser cut for a flap created to expose the stroma in photoablative refractive surgery. FIG. 7A shows a regular pattern, here a square comprising a series of cut points shown in a Cartesian grid pattern. In this case, a non-edge, non-corner photodisruption point has four closest neighbors, and distance between, for example, points diagonal from one another is longer than points laterally or vertically separated. Position errors can be an issue with the arrangement of FIG. 7A.

FIG. 7B illustrates a triangular or hexagonal distribution of photodisruption points. In FIG. 7B, a triangular cutting pattern is presented, and use of such a triangular photodisruption point pattern effectively reduces issues related to position errors. Cutting using the triangular/hexagonal arrangement of FIG. 7B provides a closer proximity of nearest neighbor photodisruption points, decreasing issues of improper cuts when the patient moves.

The design of FIGS. 7A and 7B again begin with a baseline pattern of photodisruption points and provide an additional quantity of photodisruption points intended to decrease positional errors. In the arrangement of FIGS. 7A and 7B, the photodisruption points do not include the original pattern with additional photodisruption points added, as in previous embodiments, but instead include an increased number of photodisruption points in an equivalent area.

The present design is therefore an apparatus and method for performing ophthalmic laser surgery using a pulsed laser beam, wherein the method comprises establishing an initial cutting pattern comprising a plurality of original photodisruption points, and establishing an enhanced cutting pattern comprising a plurality of enhanced photodisruption points, the plurality of enhanced disruption points selected to decrease potential adverse effects due to patient movement and having increased density over a fixed area than the plurality of original photodisruption points. The apparatus or method further includes performing an ocular surgical procedure according to the enhanced cutting pattern. Each photodisruption point comprises a laser target point. Examples of cutting patterns may include circular cuts around the periphery of a capsule, vertical side cuts for lens fragmentation, raster lamellar cuts, and grid lamellar cuts.

For example, in the vertical side cut arrangement, the method directs the pulsed laser beam to make a vertical side cut thereby creating a flap, the vertical side cut traversing a plurality of generally diagonal paths according to the enhanced fragmentation cutting pattern. Each photodisruption point in the initial fragmentation cutting pattern and the enhanced fragmentation cutting pattern comprises a laser target point, and wherein the vertical side cut traversing the plurality of generally diagonal paths provides an increased length scanning pattern relative to a cut made according to the initial fragmentation cutting pattern.

Alternately, the present design comprises an apparatus for performing an ocular laser surgical procedure based on an initial cutting pattern comprising a plurality of original photodisruption points. The apparatus comprises a laser system configured to emit a pulsed beam, optical elements configured to focus the pulsed beam emitted by the laser at a desired position on an eye of a patient, and a controller configured to control the laser and the optical elements, wherein the controller is configured to use an enhanced cutting pattern comprising a plurality of enhanced photodisruption points selected to decrease potential adverse effects due to patient movement and has increased density over a fixed area as compared with the plurality of original photodisruption points. Each photodisruption point in the initial cutting pattern and the enhanced cutting pattern comprises a laser target point. Examples of cutting patterns may again include circular cuts around the periphery of a capsule, vertical side cuts for lens fragmentation, raster lamellar cuts, and grid lamellar cuts, but other patterns or scans may be used.

In either the method or the apparatus, the plurality of enhanced photodisruption points may comprise a non-zero percentage of the plurality of original photodisruption points, or the plurality of enhanced photodisruption points may comprise none of the plurality of original photodisruption points.

An apparatus implementing the techniques or circuits described herein may be a stand-alone device or may be part of a larger device or system. In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

This disclosure has been provided in an exemplary form with a certain degree of particularity, and describes the best mode contemplated of carrying out the invention to enable a person skilled in the art to make or use embodiments of the invention. Those skilled in the art will understand, however, that various modifications, alternative constructions, changes, and variations can be made in the apparatus, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

The invention claimed is:

1. An apparatus for performing an ocular laser surgical procedure, comprising:
    a laser configured to emit a beam;
    optical elements configured to focus the beam emitted by the laser at a desired focus position on an eye of a patient; and
    a controller configured to control the laser and the optical elements, wherein the controller is configured to use a cutting pattern to control the laser and the optical elements to scan the focus position in an oscillating manner along an axial direction of the eye and to simultaneously move the focus position around a periphery of a capsule of the eye, the cutting pattern comprising a plurality of photodisruption points forming a generally circular cut with a sine wave shape in a side view around the periphery of the capsule of the eye;
    wherein each photodisruption point in the cutting pattern comprises a laser target point.

2. The apparatus of claim 1, wherein the cutting pattern extends from a start point continuously in an angular direction to an end point covering an angular range greater than 360 degrees, and wherein a starting portion and an ending portion of the cutting pattern overlap with each other.

* * * * *